United States Patent [19]

Senturia

[11] 4,316,140
[45] Feb. 16, 1982

[54] CHARGE-FLOW TRANSISTORS

[75] Inventor: Stephen D. Senturia, Boston, Mass.

[73] Assignee: Massachusetts Institute of Technology, Cambridge, Mass.

[21] Appl. No.: 76,037

[22] Filed: Sep. 17, 1979

[51] Int. Cl.³ .................... G01N 27/00; H01L 29/78; H01L 29/84

[52] U.S. Cl. ................................ 324/71 SN; 357/23; 357/25

[58] Field of Search ............... 324/71 SN; 357/23, 25, 357/26

[56] References Cited

U.S. PATENT DOCUMENTS 4,103,227 7/1978 Zemel ........................... 324/71 SN

OTHER PUBLICATIONS

Senturia et al.; "The Charge-Flow Transistor . . ."; Applied Physics Letters; vol. 30; No. 2; Jan. 15, 1977; pp. 106-108.

Primary Examiner—Ernest F. Karlsen
Attorney, Agent, or Firm—Arthur A. Smith, Jr.; Thomas J. Engellenner

[57] ABSTRACT

A charge-flow transistor having a source region and a drain region in a semiconductor substrate, a gate insulator and a gapped gate electrode with a gap material having some electrical conductance disposed in the gap thereof.

10 Claims, 3 Drawing Figures

CHARGE-FLOW TRANSISTORS

The present invention relates to charge-flow transistors.

Attention is called to Letters Patent of the present inventor U.S. Pat. No. 4,158,807 issued June 19, 1979; U.S. Pat. No. 4,209,796, issued June 24, 1980; and U.S. Pat. No. 4,236,121 issued Nov. 25, 1980, as well as the art of record therein. All are assigned to the Massachusetts Institute of Technology, the present assignee, as is, also, Ser. No. 76,038 filed Sept. 17, 1979.

A charge-flow transistor (CFT) of the type described in the above-identified patent and patent applications is a field effect device in which the gate thereof is formed of conductive fingers with a gap material (also called "gate material" herein) between the fingers. The gap material has some electrical conductance but its conductance is much less than the conductance of the conductive fingers. The conductance of the gap material and, hence, information with respect to the conduction process in the gap material can be inferred, as noted in said U.S. Pat. No. 4,158,807, from the electrical characteristics of the device. The electrical device characteristics may be measured or monitored to note changes in the conductance of the gap material that arise from changes in the environment in which the charge-flow transistor is located, for example, to sense smoke, humidity, temperature and changes therein or other environmental conditions which affect the conduction process (and hence the conductance) of the gap material. Alternatively, such changes in conductance may arise from physical processes, such as chemical reactions that may take place within the gap material. In either event, such changes in conductance can be bulk conductance changes or surface conductance changes.

Typically, when the CFT is functioning as a sensor of a condition of the environment around that CFT, the gap material should be a thin film to reduce the time needed for the transistor to react to changes in that environment, as well as to increase the magnitude of reaction within the CFT. This is so because the CFT senses effects in the electrically sensitive region or channel region thereof, as later discussed in some detail; those effects at the electrically sensitive region, in turn, are occasioned by charge distibution at or near the interface between the gap material and the gate insulator of the CFT and the charge distribution is affected by changes in the conductance of the gap material. A thin film generally permits faster (and greater) reaction on the part of the CFT.

On the other hand, if it is a condition of the gap material itself that is to be detected, then the gap material need not, and often preferably will not, be a thin film. Such condition might, for example, be a chemical reaction occurring in the gap material, wherein the rate at which the chemical reaction progresses might be important to know.

While many other uses can be thought of, one further example only is noted. It is often important to know (in semiconductor device technology, for example) if a particular material is useful as a moisture barrier material. The efficacy can be determined by forming a CFT with the material of interest as a gap material and noting the quantum of moisture that reaches the interface between the gap material and the gate insulator of the CFT. That quantum can be inferred in terms of the turn-on time or turn-off time of the CFT herein disclosed, for example, in the manner later discussed.

It is an object of the present invention to provide a charge-flow transistor in which conduction therein is mostly controlled by properties of the gap material thereof and conditions which affect the gap material.

Another object of the present invention is to provide a charge-flow transistor in which both the TURN-ON time and the TURN-OFF time thereof depend primarily on the electrical properties of the gap material thereof.

Still another object is to provide the charge-flow transistor in the context of electrical circuitry which permits sensing of the properties of the environment in which the charge-flow transistor is found from said electrical properties and changes therein.

A further object is to provide a charge-flow transistor in the context of electrical circuitry which permits the electrical properties, and, hence, the conduction process of the gap material, to be inferred.

A still further object is to provide a charge-flow transistor which, in appropriate circuitry, permits determination of the precise amount of electrical charge needed to bias the transistor to be determined to allow very accurate measurements of said electrical properties.

These and still further objects are addressed hereinafter.

The foregoing objects are achieved, generally, in a charge-flow transistor that comprises a semiconductor substrate with an electrically sensitive region or channel region in the substrate between the source region and drain region thereof, a source region, a drain region, and gapped gate electrode means comprising a pair of interconnected highly conductive fingers with a gap between the fingers. A weakly conductive gap material is disposed in the gap and is electrically connected with the conductive fingers to permit charge flow in the gap material to control electric current flow in the channel. A gate insulator is sandwiched between the gap material and the electrically sensitive region; the gate insulator covers the whole of the electrically sensitive region, said electrically sensitive region being sensitive to any electric field bias applied through the gate insulator. The width of the gap between the interconnected fingers is greater than the length of the electrically sensitive region or channel region and no part of the highly conductive fingers or the interconnection therebetween overlaps the electrically sensitive region or channel region so that both the TURN-ON time and the TURN-OFF time thereof is determined primarily by the electrical properties of the gap material.

In one embodiment, a sampling electrode is provided in the form of a conductive pad (that covers the electrically sensitive region) sandwiched between the gap material and the gate insulator to assure that the field applied through the gate insulator is uniform across the electrically sensitive region. The charge-flow transistor is shown in the context of electrical circuitry that operates to infer electrical properties of the gap material from electric current flow in the channel between the source region and the drain region thereof, said electrical properties being a function of the electrical characteristics of the gap material but being affected either by the environment within which the transistor is located or by changes within the gap material resulting from intrinsic changes such as chemical reactions. Broadly, the present invention is directed to providing a charge-flow transistor in which both the TURN-ON time and the TURN-OFF time are controlled by the electrical properties of the gap (or gate) material. The CFT is also placed in the context of an instrument.

The invention is hereinafter described with reference to the accompanying drawing in which.

Figure 1:
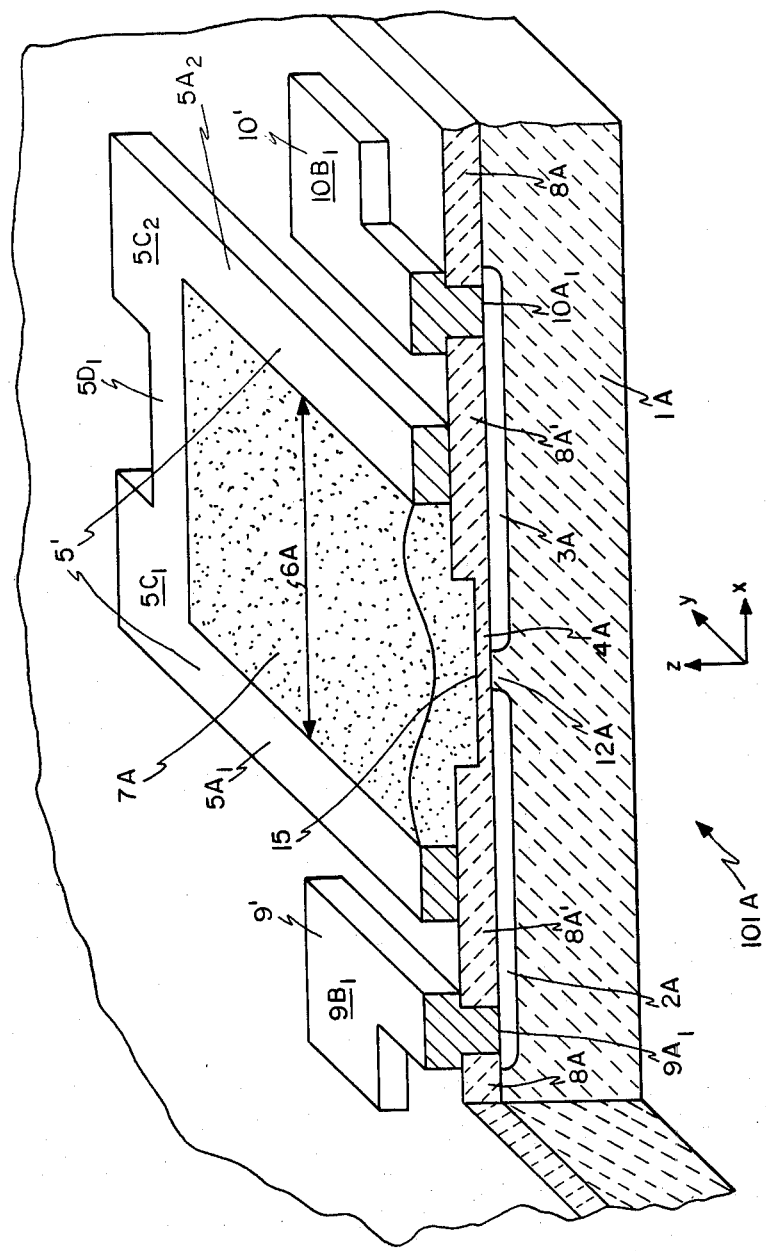
FIG. 1 is an isometric view, greatly enlarged and partly cutaway, showing a charge-flow transistor embodying the present concept.

Turning now to FIG. 1, a charge-flow transistor is shown at 101A comprising a semiconductor substrate 1A, a source region 2A, a drain region 3A, a gate insulator 4A, and a gapped gate electrode 5' comprising a pair of highly conductive fingers $5A_1$ and $5A_2$ with a gap 6A between the fingers. A gap material 7A is disposed within the gap 6A.

The device 101A is, of course, a small, flat semiconductor slab or wafer into which has been diffused impurities, to create the source region and the drain region. These regions are often fabricated in identical fashion and are, in such a case, electrically equivalent as to function. The gate 5' has a yoke $5D_1$ connecting the fingers $5A_1$ and $5A_2$ and the fingers can be connected together at their free ends to provide electrical shielding from parasitic currents (see said U.S. Pat. No. 4,209,796). The upper surface of the slab is covered by thin insulators 8A and 8A', except for the portions thereof in electrical contact with a source contact $9A_1$ of a source electrode 9', a drain contact $10A_1$ of a drain electrode 10', and the gate insulator 4A which is disposed between the sensor material 7A and the substrate 1A. Pads $9B_1$, $5C_1$ and $5C_2$, and $10B_1$ permit electrical contact to the source, gate and drain, respectively, of the device 101A, as is well known. The pads are isolated from the substrate by the insulating layers 8A and 8A' which serve to insulate the contacts or electrodes 5', 9' and 10' from the substrate 1A and from each other. The gate insulator 4A can be a thin silicon dioxide layer. The insulators 8A and 8A' can also be a silicon dioxide layer but must be thicker than gate insulator 4A. Throughout this explanation, the terms "source" and "drain" are used to designate the electrical connection to the source region of the charge-flow transistor and the drain region thereof, respectively, as is done with respect to conventional MOS devices, as well as the respective region. The term "gate" is employed in its usual context.

There is a detailed explanation in said U.S. Pat. No. 4,158,807 of the various forms that the charge-flow transistor can take: it may be an enhancement mode p-channel device in which there is no conduction in the electrically sensitive region or channel region labeled 12A in the absence of an appropriate bias; or it may be a depletion mode n-channel device in which there is no conduction in the electrically sensitive region or channel region 12A in the presence of an appropriate bias. Herein the explanation is directed to the structure to apply the appropriate bias to the device, rather than the precise type of device used, that is, whether electrons or holes provide current flow in the region 12A or whether the transistor be an enhancement or depletion mode device. It should be noted at this juncture that the electrically sensitive region or channel region 12A when the transistor 101A is biased ON is known as a channel; also, biasing is achieved by virtue of an electric field through the gate insulator 4A (in the z-direction in FIG. 1) by virtue of charge carrier distribution in the gap material 7A at and around the interface shown at 15 between the gap material 7A and the gate insulator 4A.

Figure 2:
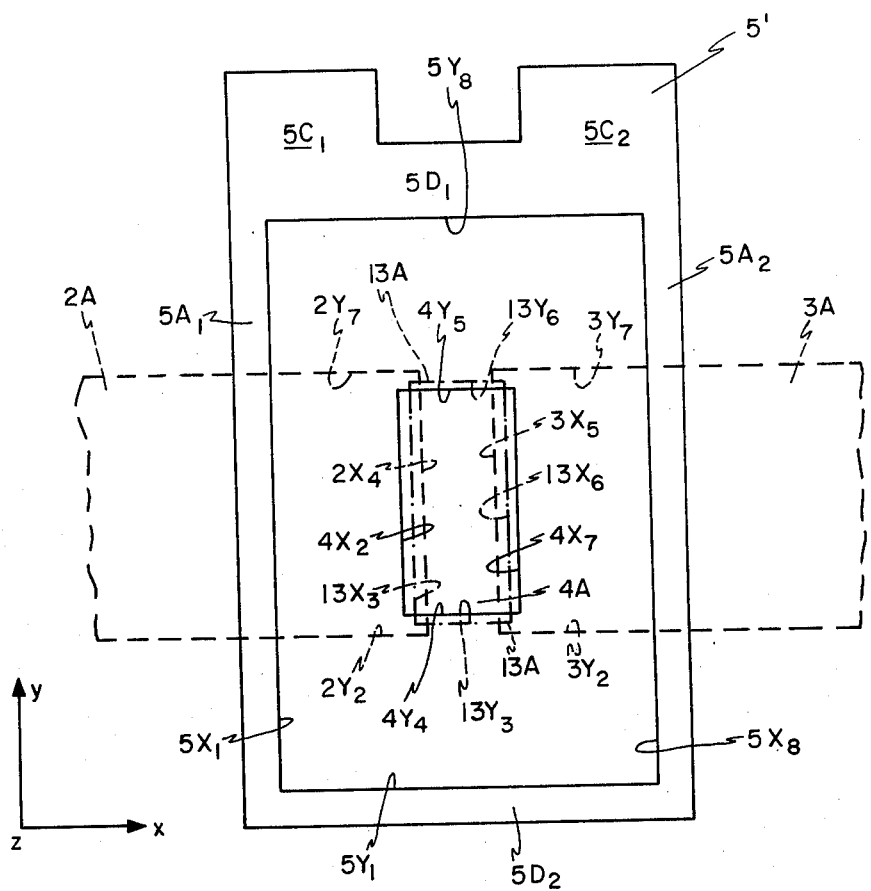
FIG. 2 is an enlarged plan-view of a portion of the charge-flow transistor of FIG. 1, in which the gap material is not shown, but which includes a sampling electrode not shown in FIG. 1.

Because the relative positions of the boundaries of various regions are critical to the description (and operation) of the device, there is shown in FIG. 2 an enlarged plan-view of a portion of the charge-flow transistor 101A of FIG. 1, in which the gap material 7A has been omitted, but which includes a sampling electrode 13A and a second connective yoke $5D_2$, not shown in FIG. 1. The extent of the electrically sensitive region, i.e., the channel region 12A, can be described with reference to FIG. 2. The boundaries of the electrically sensitive region are that edge of the source region 2A denoted $2X_4$, the projection into the substrate of those edges of the gate insulator 4A denoted by $4Y_4$ and $4Y_5$, and that edge of the drain region 3A denoted by $3X_5$.

The connective yokes $5D_1$ and $5D_2$ provide electrical connection between the gate fingers $5A_1$ and $5A_2$ and serve to shield the electrically sensitive region, as described in said U.S. Pat. No. 4,158,807. The critical relative locations of features of the device can be described as follows. With reference to the x-axis shown in FIG. 2, the relative order of the x positions (i.e., positions in the x-direction from left to right) of the labeled edges is: that edge of the gate finger $5A_1$ denoted by $5X_1$; said gate insulator edge $4X_2$; said source region edge $2X_4$; said drain region edge $3X_5$; said gate insulator edge $4X_7$; and that edge of gate finger $5A_2$ denoted $5X_8$. With reference to the y-axis shown in FIG. 2, the relative order of the y positions (i.e., the positions in the y-direction from bottom toward the top in FIG. 2) of the labeled edges is: in any order, that edge of the yoke $5D_2$ denoted by $5Y_1$, that edge of the source region 2A denoted $2Y_2$, and that edge of drain region 3A denoted $3Y_2$; said gate insulator edge $4Y_4$; said gate insulator edge $4Y_5$; and, in any order, that edge of the source region 2A denoted $2Y_7$ and that edge of drain region 3A denoted by $3Y_7$, and that edge of gate electrode 5' denoted $5Y_8$. In some embodiments of the present invention, it may be useful to add a sampling electrode 13A (shown in broken-line form in FIG. 2 ), comprising a highly conductive island pad sandwiched between gate insulator 4A and gap material 7A of FIG. 1. The x- and y-positions of the boundaries of such a sampling electrode are shown at $13X_3$, $13Y_6$, $13X_6$, and $13Y_3$ in FIG. 2. The positions of these edges relative to the other designated edges are not critical. Those positions shown in FIG. 2, namely $13Y_3$ and $13Y_6$ outside the boundaries $4Y_4$ and $4Y_5$, respectively, and $13X_3$ and $13X_6$ outside the boundaries $2X_4$ and $3X_5$, respectively, assure that electric field between the gap material 4A and the electrically sensitive region 12A is made uniform across the entire electrically sensitive region 12A by the presence of sampling electrode 13A, a property that is useful in quantitative studies of conductive processes and bias changes in gap material. It should be further noted that any charge carrier movement between the sampling electrode 13A and the gate electrode 5' is through or on the gap material 7A.

The gap material 7A in FIG. 1 is electrically connected with the gapped gate electrode 5' in order to permit charge-flow in the gap material 7A to control electric current flow in the electrically sensitive region or channel region 12A. It is noted above that the gap material 7A is only weakly conducting (typically the electrical conductance of gap material, expressed in sheet conductance, is greater than about $10^{-17}$ (ohm/square)$^{-1}$ with an upper limit of electrical conductance at about $10^{-6}$ (ohms/square)$^{-1}$, whereas the fingers $5A_1$ and $5A_2$ may be aluminum which is highly conducting. In this situation, a voltage applied to the fingers $5A_1$ and $5A_2$ will evoke charge flow across or through the gap material 7A, which charge flow serves to bias the device 101A. The rate at which such charge flow progresses from the fingers $5A_1$ and $5A_2$ to the part of the gap material 7A at the opposite side of the gate insulator 4A from the electrically sensitive region or channel 12A is a function of the electrical properties of the gap material; and those electrical properties are a function of the inherent electrical characteristics of the gap material and the effect of the environment thereon. The electrical properties of the material 7A primarily determine TURN-ON ("$t_{on}$" herein) of the device 101A. However, when the fingers $5A_1$ and $5A_2$ are outside the electrically sensitive region or channel region 12A, as they are in the device 101A, then the electrical properties of the gap material primarily also determine the TURN-OFF time ("$t_{off}$" herein) of the device 101A, and, indeed, in the device 101A $t_{on} \approx t_{off}$, that is, $t_{on}$ and $t_{off}$ are about within an order of magnitude of each other. Said another way, no part of the highly conductive portions of the gate 5' (i.e., the fingers $5A_1$ and $5A_2$ and the conductive yokes $5D_1$ and $5D_2$ connecting the free ends of the fingers $5A_1$ and $5A_2$ which typically are aluminum patterns at the surface of the transistor) overlap the electrically sensitive region or channel region 12A. Thus, in the CFT 101A, both times $t_{on}$ and $t_{off}$ represent significant delays in switching the CFT, delays far greater than conventional FETs which switch in times typically less than microseconds.

With the exception of the techniques for fabricating the gapped gate electrode filled with a thin-film or other gap material 7A, the fabrication procedures for n-channel and p-channel charge-flow transistors and for enhancement-mode and depletion mode charge-flow transistors are based on well-established art, using many of the same techniques widely used in the manufacture of MOSFETs (metal-oxide-semiconductor field-effect transistors) and MOS integrated circuits, as is discussed in said U.S. Pat. No. 4,158,807.

Two polymers that are useful as gap material 7A for combustion-product sensors are poly (Shiff's base) from p-phenylene diamine and thiophene-2,5-diacarboxaldehyde, and poly (imidazole) from 1,4-bis (phenylglyoxyoyl) benzene and ferrocene-1,1' diacarboxaldehyde. With either, the thickness of the polymer film typically is in the range from about 1000 Å (thin-film) to 10,000 Å. It is not necessary to remove the polymer from the rest of the wafer as it has little influence on device operation except for that portion of the film disposed in the gap 6A.

Other gap or gate materials include classes of materials consisting essentially of: organic polymers, metal oxides, oxide glasses, chalcogenide glasses and other amorphous inorganic semiconductors. In this connection, the glasses can perform the dual function of sensing and passivation.

The semiconductor substrate of the transistor 101A may be taken from the group of materials consisting essentially of silicon; germanium; silicon carbide; gallium arsenide or related materials of the class known as III-V compounds; and cadmium telluride and related materials of the class known as II-VI compounds.

Other properties to be sensed include gas or vapor or a combination of gases or vapors; the presence of free radicals; the presence of water vapor; the presence of electromagnetic radiation, including microwave, infrared, visible light, ultraviolet light, X-rays, or gamma rays; the presence of subatomic particles, such as beta particles, alpha particles, neutrons; the presence of atomic or molecular beams; changes in ambient pressure; changes in ambient temperature; the chemical composition of a solution; and the electrochemical potential of a solution.

The charge-flow transistor herein disclosed typically has metallization to reduce the detrimental effect of parasitic currents that flow within the transistor, as is discussed in detail in said U.S. Pat. No. 4,209,796, and the further techniques disclosed in the earlier application can be used with the present device. Also, the present transistor can be used in the various logic and oscillator configurations of said U.S. Pat. No. 4,236,121.

Figure 3:
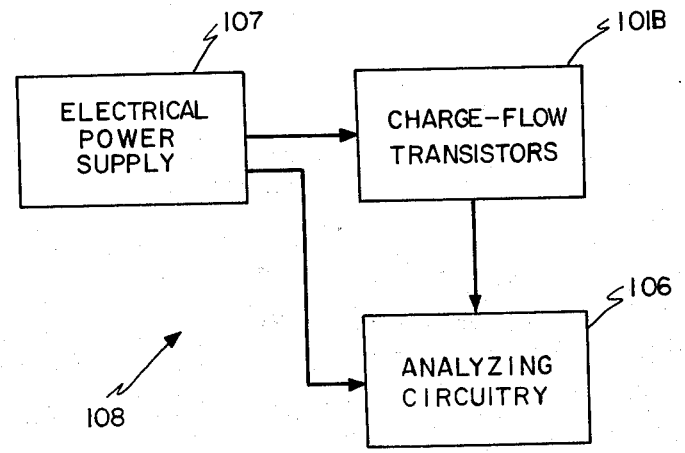
FIG. 3 is a diagrammatic representation of an instrument embodying a charge-flow transistor (or a plurality of charge-flow transistors) of the type shown in FIG. 1.

The diagrammatic showing in FIG. 3 represents an instrument 108 that includes one or more charge-flow transistors 101B, (like the transistor 101A) an electric power source 107 to bias the one or more charge-flow transistors 101B, and analyzing circuitry to detect and analyze electric current flow in the channels of the one or more charge-flow transistors 101B. For present purposes, it can be assumed that the block 101B can include, for example, appropriate circuitry to form one or more logic elements and, perhaps, one or more oscillators; see said U.S. Pat. No. 4,236,121 as well as the patent application that accompanies herewith. The analyzing circuitry 106 is connected to sense the TURN-ON time $t_{on}$ of the transistor 101B and the TURN-OFF time $t_{off}$ thereof and is operable to relate the times $t_{on}$ and $t_{off}$ to at least one electrical property of the gap material of the transistor 101A.

Some comments of a general nature are contained in this paragraph. On the basis of the above-discussion, it will be appreciated that biasing of the electrically sensitive region 12A both ON and OFF (respectively to form and remove a conductive channel between the source 2A and the drain 3A) is accomplished substantially totally by the electrical charge pattern in the gap material (or gate material) 7A at or near the interface 15. Hence, the critical consideration here is flow of electrical charges to, from and in or on the gate material 7A. That charge flow can be sensed or monitored to provide information as to the environment around the transistor 101A, but it can provide, as well, information as to other conditions within the gate material 7A. The gate 5' has fingers, a yoke, and can have a metallization at the free ends of the fingers, as noted above. Conceptually, however, other gate configurations and metallization patterns can be employed, it being kept in mind, that the important issue here is charge flow to and from the interface 15 between the gate material 7A and the gate insulator 4A, for it is what happens electrically at that interface which determines electrical current patterns between the source 2A and the drain 3A of the charge-flow transistors 101A. Furthermore, in accordance with the present teachings, it is possible to control to some extent the time relationship between $t_{on}$ and $t_{off}$ to fit particular requirements.

Further modifications of the invention herein disclosed will occur to persons skilled in the art and all such modifications are deemed to be within the spirit and scope of the invention as defined by the appended claims.

What is claimed is:

1. A charge-flow transistor comprising a semiconductor substrate, a source region in the substrate, a drain region in the substrate, and electrically sensitive region in the substrate between the source region and the drain region, gate means comprising a pair of interconnected highly conductive fingers with a gap between the fingers and a gap material having much less conductance than the highly conductive fingers disposed in said gap, said gap material being electrically connected to the highly conductive fingers to permit charge flow therebetween, a gate insulator sandwiched between the gap material and the electrically sensitive region, said electrically sensitive region being electrically sensitive to any bias electric field applied through the gate insulator, said bias electric field being created in said charge-flow transistor substantially totally by charge patterns in the gap material at and near the interface between the gap material and the gate insulator to provide a charge-flow transistor whose TURN-ON time $t_{on}$ is about equal to the TURN-OFF $t_{off}$ thereof.

2. A charge-flow transistor as claimed in claim 1 in which the gate means includes a highly conductive yoke interconnecting the highly conductive fingers.

3. A charge-flow transistor as claimed in claim 2 wherein the yoke and the fingers are metallized pattern, no part of the metallized pattern overlaying said electrically sensitive region.

4. A charge-flow transistor as claimed in claim 1 wherein the gate means includes a highly conductive yoke interconnecting each end of one highly conductive finger to the corresponding end of the other highly conductive finger to form a highly conductive pattern surrounding the gap material to shield the gate material from parasitic currents.

5. An instrument that includes a charge-flow transistor as claimed in claim 1 and that further includes means connected to bias the charge-flow transistor to cause electric current flow in the electrically sensitive region between the source region and the drain region and to effect TURN-ON and TURN-OFF of the transistor, and electrical circuitry connected to sense the TURN-ON time $t_{on}$ and the TURN-OFF time $t_{off}$ and to relate the same to at least one electrical property of said gap material.

6. An instrument that includes a charge-flow transistor and that further includes means connected to bias the charge-flow transistor to effect TURN-ON and TURN-OFF thereof and electrical circuit means connected to sense the TURN-ON time $t_{on}$ of the transistor and TURN-OFF $t_{off}$ thereof, said charge-flow transistor comprising a semiconductor substrate, a source region in the substrate, a drain region in the substrate, an electrically sensitive region in the substrate between the source region and the drain region, gate means comprising a highly conductive member and a gate material having much less conductance than the highly conductive member, said gate material being electrically connected to the highly conductive member to permit charge-flow therebetween, a gate insulator bridging the electrically sensitive region in the substrate between the source region and the drain region, the gate insulator being sandwiched between the gate material and the electrically sensitive region which is sensitive to any bias electric field applied through the gate insulator, said bias electric field being created in said charge-flow transistor substantially totally by charge patterns in the gate material in the part thereof adjacent the gate insulator, no part of said highly conductive member overlaying said electrically sensitive region to provide a transistor in which the time $t_{on}$ is about equal to the time $t_{off}$, said electrical circuit means being operable to relate the magnitude of the times $t_{on}$ and $t_{off}$ to a property of said gap material.

7. A charge-flow transistor as claimed in claim 6 wherein the TURN-ON time $t_{on}$ and the TURN-OFF $t_{off}$ are within about an order of magnitude of each other.

8. A charge-flow transistor comprising a semiconductor substrate, a source region in the substrate, a drain in the substrate, an electrically sensitive region in the substrate between the source region and the drain region, gate means comprising a pair of interconnected highly conductive fingers and a gate material having much less conductance than the highly conductive fingers, said gate material being electrically connected to the highly conductive fingers to permit charge flow therebetween, a gate insulator bridging the electrically sensitive region in the substrate between the source region and the drain region, the gate insulator being sandwiched between the gate material and the elctrically sensitive region, said electrically sensitive region being electrically sensitive to any bias electric-field applied through the gate insulator, said bias electric-field being created in said charge-flow transistor substantially totally by charge patterns in the gate material in the part thereof adjacent the gate insulator, no part of said highly conductive portions of the gate means overlaying said electrically sensitive region.

9. A charge-flow transistor as claimed in claim 8 which further includes a sampling electrode, comprising a highly conductive island pad sandwiched between the gate insulator and the gate material, positioned on the opposite side of the gate insulator from the electrically sensitive region, any charge carrier movement between the sampling electrode and the gate means being through or on the gate material.

10. A charge-flow transistor comprising a semiconductor substrate, a source region in the substrate, a drain in the substrate, an electrically sensitive region in the substrate between the source region and the drain region, gate means comprising a highly conductive member and a gate material having much less conductance than the highly conductive member, said gate material being electrically connected to the highly conductive member to permit charge flow therebetween, a gate insulator, a sampling electrode, comprising a highly conductive island pad sandwiched between the gate insulator and the gate material, positioned on the opposite side of the gate insulator from the electrically sensitive region, any charge carrier movement between the sampling electrode and the gate means being through or on the gate material, said electrically sensitive region being electrically sensitive to any bias electric field applied through the gate insulator, said bias electric field being created in said charge-flow transistor substantially totally by charge patterns in the sampling electrode at and near the interface between the sampling electrode and the gate insulator.

* * * * *